US006221315B1

(12) United States Patent
Giesler et al.

(10) Patent No.: US 6,221,315 B1
(45) Date of Patent: Apr. 24, 2001

(54) APPARATUS FOR SEPARATION OF BIOLOGIC COMPONENTS FROM HETEROGENEOUS CELL POPULATIONS

(75) Inventors: Richard Giesler, Deerfield; John R. Chapman, Lake Villa; Dale R. Ellis, Wonder Lake; Daniel F. Bischof, McHenry, all of IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/290,653

(22) Filed: Apr. 12, 1999

Related U.S. Application Data

(62) Division of application No. 08/467,818, filed on Jun. 6, 1995, now Pat. No. 5,916,743, which is a division of application No. 08/255,107, filed on Jun. 7, 1994, now Pat. No. 5,641,622, which is a continuation of application No. 08/069,077, filed on May 28, 1993, now abandoned, which is a continuation-in-part of application No. 07/965,547, filed on Oct. 23, 1992, now abandoned, which is a continuation of application No. 07/582,288, filed on Sep. 13, 1990, now abandoned.

(51) Int. Cl.$^7$ ...................................................... B01L 11/00
(52) U.S. Cl. ............................... 422/101; 422/64; 422/72; 422/186.01; 436/45; 436/518; 436/177; 436/526; 436/180; 494/1; 494/5; 494/10; 494/23; 494/27; 494/43; 494/49; 494/56; 210/222; 210/223; 210/360.1; 210/380.1; 210/295
(58) Field of Search ..................................... 210/222, 223, 210/360.1, 380.1, 295; 422/64, 72, 101, 186.01; 436/45, 518, 177, 526, 180; 494/1, 5, 10, 23, 27, 43, 49, 56

(56) References Cited

U.S. PATENT DOCUMENTS

| | | | |
|---|---|---|---|
| Re. 32,056 | 12/1985 | Granzow et al. ........................ 141/1 |
| 3,999,945 | * 12/1976 | Kushner et al. ........................ 23/253 |
| 4,035,316 | 7/1977 | Yen et al. ........................ 260/2.5 B |
| 4,146,172 | * 3/1979 | Cullis et al. ........................... 233/26 |
| 4,415,665 | 11/1983 | Mosbach et al. ..................... 435/179 |
| 4,474,877 | 10/1984 | Imagawa et al. ........................ 435/5 |
| 4,526,515 | 7/1985 | DeVries ................................. 417/63 |
| 4,612,007 | 9/1986 | Edelson . |
| 4,624,923 | 11/1986 | Margel ................................. 435/176 |
| 4,692,411 | * 9/1987 | Ghose ................................. 435/243 |
| 4,695,553 | 9/1987 | Wardlaw et al. ..................... 436/177 |
| 4,710,472 | * 12/1987 | Saur et al. ........................... 435/287 |
| 4,722,790 | 2/1988 | Cawley et al. . |
| 4,734,089 | 3/1988 | Cullis ..................................... 494/45 |
| 4,747,952 | 5/1988 | Nakano et al. . |
| 4,752,563 | 6/1988 | Kotright et al. ........................... 435/2 |
| 4,783,336 | * 11/1988 | Margel et al. ........................ 424/462 |
| 4,797,475 | 1/1989 | Terasaki et al. ...................... 530/387 |
| 4,818,418 | 4/1989 | Saunders ............................. 210/782 |
| 4,861,705 | 8/1989 | Margel ................................... 435/2 |
| 4,927,749 | * 5/1990 | Dorn ...................................... 435/2 |
| 4,935,147 | * 6/1990 | Ullman et al. ........................ 210/695 |
| 5,017,472 | 5/1991 | Bankert et al. ....................... 436/824 |
| 5,091,206 | 2/1992 | Wang et al. . |
| 5,116,724 | 5/1992 | Delaage et al. ........................... 435/2 |
| 5,225,353 | 7/1993 | Berenson et al. ........................ 435/2 |
| 5,238,812 | * 8/1993 | Coulter et al. ........................ 435/7.2 |
| 5,246,829 | 9/1993 | Delaage et al. ........................... 435/2 |
| 5,248,589 | 9/1993 | Bose et al. ............................... 435/2 |
| 5,536,475 | 7/1996 | Moubayed et al. . |

OTHER PUBLICATIONS

Dooley, D.C., Law, P. and Alsop, P., "A New Density Gradient for the Separation of Large Quantities of Rosette–Positive and Rosette–Negative Cells," *Experimental Hematology*, vol. 15, pp. 296–303 (1987).

Hirn–Scavennec, J. et al., "Elimination of Leukemia Cells From Human Bone Marrow Using Floating Beads," *Transplantation*, vol. 46, No. 4, pp. 558–563 (1988).

Koistinen, P., "Human Peripheral Blood and Bone Marrow Cell Separation Using Density Gradient Centrifugation on Lymphoprep and Percoll in Hematological Diseases," *Scan. J. Clinc. Lab. Invest.*, vol. 47, pp. 709–714 (1987).

Cambier, J.C. and Neale, M.J., "Isolated Phosphorylcholine Binding Lymphocytes. I. Use of a Cleavable Crosslinking Reagent for Solid–Phase Adsorbent Isolation of Functional Antigen Binding Cells," *Journal of Immunological Methods*, vol. 51, pp. 209–221 (1982).

Bonnafous, J. et al., "Cell Affinity Chromatography with Ligands Immobilized Through Cleavable Mercury–Sulfur Bonds," *Journal of Immunological Methods*, vol. 58, pp. 93–107 (1983).

Bankhurst, A.D. and Williams, R.C., Jr., "Identification of DNA–Binding Lymphocytes in Patients with Systemic Lupus Erythematosus," *Journal of Clinical Investigation*, vol. 56, pp. 1378–1385 (Dec. 1975).

Aizawa, S. and Tavassoli, M., "Molecular Basis of the Recognition of Intravenously Transplanted Hemopoietic Cells by Bone Marrow," *Proceedings of the National Academy of Sciences*, vol. 85, pp. 3180–3183 (May 1988).

(List continued on next page.)

*Primary Examiner*—Jennifer Graser
(74) *Attorney, Agent, or Firm*—Andrew G. Kolomayets; Bradford R. L. Price; Michael C. Mayo

(57) ABSTRACT

Apparatus for separating a biological component from a biological fluid are disclosed. The apparatus includes a chamber for receiving a biological fluid including a biological component, and a rotor for creating a centrifugal field within the chamber. A source of particles may be included wherein the particles have a binding site for selectively binding to the biological component. The particles may be aseptically introduced into the chamber. The apparatus may withdraw whole blood from a donor, separate the whole blood to obtain a target cell population and return a selected one of either the target cell population or at least a portion of the whole blood remainder to the donor or patient. A disposable separation inset for use in conjunction with a rotatable separation device such as the apparatus described above may also be provided.

8 Claims, 2 Drawing Sheets

OTHER PUBLICATIONS

Lasky, L.A., "Selectins: Interpreters of Cell–Specific Carbohydrate Information During Inflammation," *Science*, vol. 258, pp. 964–969 (Nov. 6, 1992).

Kiess, W. and Butenandt, O., "Effect of Enzyme and Enzyme Inhibitors on Specific Binding of hGH to Human Peripheral Lymphocytes," *Acta Endocrinologica*, vol. 109, pp. 139–144 (1985).

Smal, Jean et al., "Receptor–Binding and Down–Regulatory Properties of 22,000–MW Human Growth Hormone and Its Natural 20,000–MW Variant on IM–9 Human Lymphocytes," *Journal of Biochemistry* vol. 225, pp. 283–289 (1985).

Eshet, R., Peleg, S. and Laron, Z., "Direct Visualization of Binding, Aggregation and Internalization of Human Growth Hormone in Cultured Human Lymphocytes," *Acta Endocrinologica*, vol. 107, pp. 9–15 (1984).

Titus, J.A., Sharrow, S.O., and Segal, D.M., "Analysis of Fc (IgG) Receptors on Human Peripheral Blood Leukocytes by Dual Fluorescence Flow Microfluorometry. II. Quantitation of Receptors on Cells That Express the OKM1, OKT3, OKT4, and OKT8..Antigens," *Journal of Immunology*, vol. 130, No. 3, pp. 1152–1158 (1983).

Smith, W.B., Gamble, J.R. and Vadas, M.A., "Cytokines in the Inflammatory Response," *Interferons & Cytokines*, vol. 21, pp. 26–29 (1992).

Papayannopoulou, T., Brice, M., Broudy, V.C., and Zsebo, K.M., "Isolation of c–kit Receptor–Expressing Cells From Bone Marrow, Peripheral Blood and Fetal Liver: Functional Properties and Composite Antigenic Profile," *Blood*, vol. 78, No. 6, pp. 1403–1412 (1991).

Wright, S. et al., "CD14, a Receptor for Complexes of Lipopolysaccharide (LPS) and LPS Binding Protein," *Science*, vol. 249, pp. 1431–1433 (Sep. 21, 1990).

Lipkowitz, S. et al., "Expression of Receptors for Interleukin 2: Role in the Commitment of T Lymphocytes to Proliferate," *Journal of Immunology*, vol. 132, No. 1, pp. 31–37 (1984).

Mittal, K.K., "Standardization of the HLA Typing Method and Reagents," *Vox Sanguinis*, vol. 34, pp. 58–63 (1978).

"The 'Autopheresis–C'System" from Baxter Healthcare Corporation, Fenwal Division (1990) (Brochure).

"'CS–3000' Plus Blood Cell Separator" from Baxter Healthcare Corporation, Fenwal Division (1989) (Brochure).

"'CS–3000' Plus Blood Cell Separator" from Baxter Healthcare Corporation, Fenwal Division (1990) (Brochure).

Pharmacia Catalogue re: Percoll and Ficoll–Paque Products.

Product Insert for "LSM" Solution from Organon Teknika (1986).

"'Histopaque'–1077" from "Sigma Diagnostics" (1988) (Brochure).

Habeeb, A.F.S.A., "A Novel Preparation of Immunoadsorbents," *Biochimica et Biophysica Acta*, vol. 673, pp. 527–538 (1981).

* cited by examiner

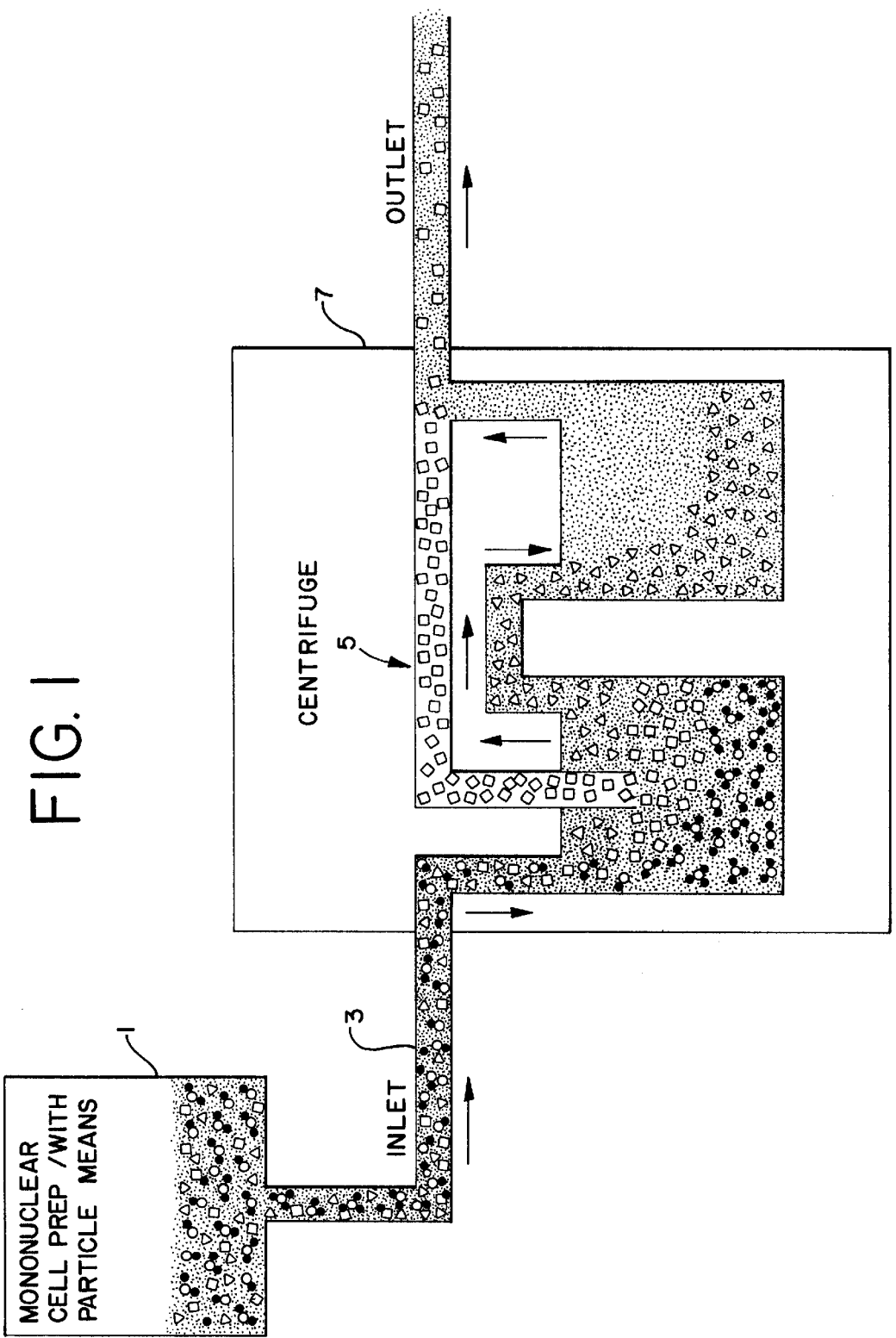

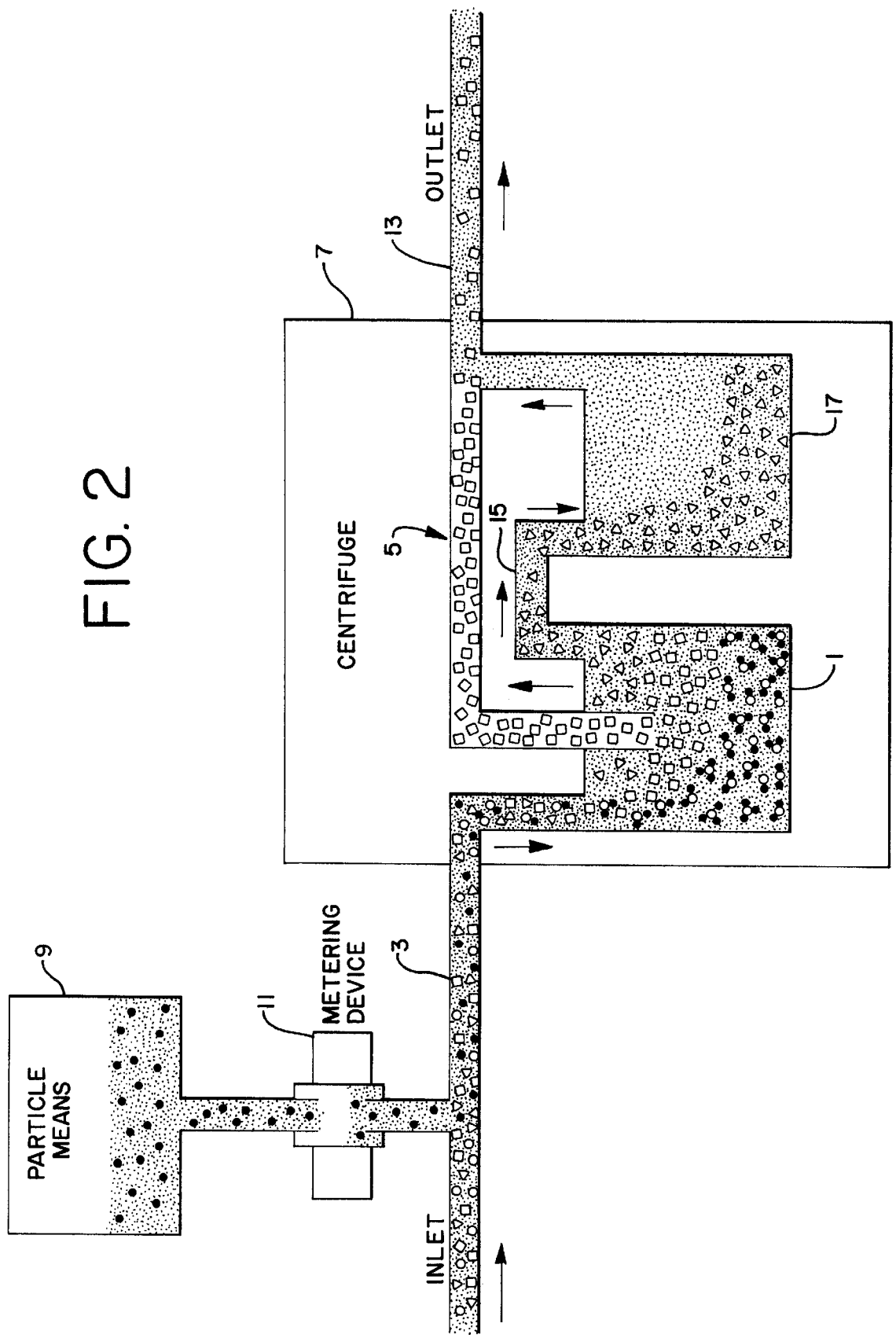

APPARATUS FOR SEPARATION OF BIOLOGIC COMPONENTS FROM HETEROGENEOUS CELL POPULATIONS

This is a divisional application of application Ser. No. 08/467,818 filed Jun. 6, 1995, now U.S. Pat. No. 5,916,743 which is a divisional application of application Ser. No. 08/255,107 filed Jun. 7, 1994, now U.S. Pat. No. 5,641,622, which is a continuation of application Ser. No. 08/069,077, filed on May 28, 1993, now abandoned, which is a continuation-in-part of application Ser. No. 07/965,547, filed on Oct. 23, 1992, now abandoned, which is a continuation of application Ser. No. 07/582,288, filed on Sep. 13, 1990, now abandoned.

TECHNICAL FIELD

The present invention concerns a novel system for separating a specific cell population from a heterogeneous cell mixture. More particularly, the invention concerns a closed, sterile continuous flow process for separating a nucleated heterogeneous cell population from a large volume of heterogeneous cell mixture in a relatively short time.

BACKGROUND OF THE INVENTION

In the field of cell separation, it is common to separate cells from plasma in blood and also to separate by centrifugation various types of. cells such as red cells from white cells, and the like. Centrifugation segregates cells according to their differing specific gravities. However, there is often a need to separate from a suspension cells having specific gravity only slightly different from those of other cells in the suspension. If the cells are of nearly equal specific gravity, they may not be separated by centrifugation.

For example, it may be desirable to isolate various types of leukocytes from a bone marrow concentrate or a peripheral blood cell concentrate. Or, it may be desirable to perform selective separation of tumor cells from a bone marrow concentrate, for example, hematopoietic progenitor cells. It may be desirable to selectively separate specific T-lymphocyte subset populations (helper-inducer or suppressor-cytotoxic T-lymphocytes) from a lymphocyte concentrate that is prepared using a blood cell separator.

Additionally, it may be desirable to selectively separate precursors of lymphokine activated killer (LAK) cells, tumor infiltration lymphocyte (TIL) cells, or activated killer monocytes, from lymphocyte or monocyte cell concentrates or from a tissue cell preparation.

By current techniques of the prior art, such as Sauer, et al, U.S. Pat. No. 4,710,472, magnetic separations in significant quantities of individual subsets of cells from larger populations became possible. This, in turn, opens up new vistas of research and therapeutic techniques, making use of the purified cell populations that may be obtained.

Another current practice in the field of cell separation, utilizes sheet membranes, hollow fibers, or packed beds of either beads or particles having physically adsorbed or covalently attached chemicals or biochemicals, such as antibodies. By these means certain populations of cells are selectively separated from whole blood, blood components, bone marrow, tissue digests, or other types of cellular suspensions. These devices are designed to allow continuous inflow and return of the cell mixtures. When used to process blood, these devices usually operate at the normal rates of blood flow and under conditions in which the concentration of desired cells can be very low compared with other cell types. The separation process, therefore, is often not efficient.

Immunoaffinity cell separation systems for blood and bone marrow conventionally require two separation processes: an initial cell separation to remove red blood cells and the immunoaffinity cell separation to capture or deplete a specific "target" cell population, such as a nucleated heterogeneous cell population. In the immunoaffinity separation step, a biological particle such as an animal erythrocyte, is modified by coupling to its surface a monoclonal or polyclonal antibody or other biological selected to specifically bind to an antigen or immunogenic marker on the surface of the target cell. A high density particle/target cell conjugate, such as an erythrocyte rosette, is thereby created. Because a significant incubation time is required for particle/cell bonding to occur in such systems, the cell mixture is usually centrifuged twice, once to promote binding of the particle-antibody conjugate to the target cell and a second time to separate the particle/target cell conjugate using a high density separation media so that only the high density erythrocytes and erythrocyte/target cell conjugates will sediment through the medium. Separation is thus effected with efficiencies of up to 95%.

In addition to the many steps required to effect immunoaffinity separations using these techniques, the immunoaffinity cell separator systems currently described in the literature are limited in the volume of cell preparations that can be processed, and none can be performed in a closed, continuous flow on-line procedure with a patient.

In view of these difficulties, the need exists for new and improved methods of continuously separating a specific cell population from a heterogeneous cell mixture, especially for separating from a cell mixture populations of cells that differ in specific gravity and/or sedimentation velocity only slightly from other cells in the mixture.

SUMMARY OF THE INVENTION

The present invention provides a method for separating biologic component from heterogeneous cell populations by the process of reacting a specific binding molecule attached to an insolubilized particle with the biologic component to alter the sedimentation velocity of the bound biologic component. The bound biologic component is then separated from unbound components by continuous centrifuging. The invention combines the advantage of centrifugating large volumes of cells in a closed, sterile continuous flow process with the high degree of selectivity provided by immunoaffinity cell separation systems. This invention is especially useful for separating a target cell population from a heterogeneous cell suspension in which the density and/or sedimentation velocity of the target cells is insufficiently differentiated from those of other cells in the suspension to effect separation by centrifugation with or without the use of high density separation media.

The processes provided herein yields a method for removing from heterogeneous cell populations—such as blood, blood components, blood substitutes, bone marrow, and tissue digests—biologic components including the following: hematopoietic cells, including all leukocyte subpopulations and pluripotent stem cells; tumor cells; tissue culture cell lines, including hybridoma cells; antigen specific lymphocytes; infectious agents, including bacteria, virus and protozoa; and toxic substances, including but not limited to drugs or pharmaceuticals and animal, microbial and plant toxins. These processes can be used for therapeutic and diagnostic applications and can be utilized to perform both positive and negative cell selections. In positive cell selection, the bonds between the captured cells and the particles are released and the isolated captured cells are the products used in therapeutic or diagnostic applications. In negative cell selection, the cell mixture depleted of the captured cells (i.e., the "target cells") is the cell product.

Like known affinity cell separation procedures, the present process uses separation particles with a specific affinity for the target cells or having chemically attached thereto a biological molecule with a specific affinity for the target cells. In a continuous flow process for conducting leukapheresis, the affinity particles are continuously fed at a predetermined ratio to the cell mixture through a mixing chamber wherein the particle/target cell conjugates are formed. From the mixing chamber the entire cell mixture, containing the particle/target cell conjugates, passes into a continuous flow centrifuge. Any of a number of commercial continuous flow centrifuges and eleutriators that employ disposable plastic insets including chamber means for facilitating density based separation can be used, such as the CS-3000® Blood Cell Separator and Autopheresis-C® System sold by the Fenwal Division of Baxter Healthcare Corporation, of Deerfield, Ill.; the 2997 sold by Cobe Laboratories Inc. of Lakewood, Colo.; and "Beckman J-Series Elutriation Centrifuges" sold by Beckman Instruments, Palo Alto, Calif.

In the Autopheresis-C® System, anticoagulated whole blood may be pumped into a separation device, where plasma is initially separated in a centrifugal density separation chamber. From there, the separated plasma is filtered through a rotating membrane filter and directed into a collection chamber. Concentrated cellular components are pumped from the density separation device to an in-line reinfusion reservoir. Undesired cellular components are returned to the donor, typically through the same needle.

The CS-3000® Blood Cell Separator employs a two-stage, centrifugal density separation and collection process. In a typical platelet collection, a depletion procedure using the CS-3000®, whole blood is withdrawn from a donor or a blood reservoir and pumped into a separation chamber, where the less dense components, (e.g. platelets and plasma) are separated from the more dense components (e.g. red blood cells). The platelet-containing plasma is transferred from the first chamber into a second chamber via one outlet port, while the red blood cells are removed from the first chamber via a second outlet port. The platelets are separated from the plasma in the second chamber by centrifugal force, and the platelet-deficient plasma is then removed, leaving platelet concentrate in the second chamber.

The model 2997 uses a generally belt-shaped disposable chamber mounted within a rotor in the centrifuge housing. In a typical procedure, whole blood is directed into the belt and, under centrifugal force, is separated into lighter and heavier components as the blood flows circumferentially through the belt. Depending on the particular configuration of the belt, and the location of pick-off points within the belt, the blood may be separated into desired components which are withdrawn from the belt. Other components may be returned to a donor or to a reservoir from which the whole blood is initially drawn.

Commercial sterile plastic insets having integral chambers, which may be used as mixing and separation chambers in accordance with the present invention, can be purchased for use with each of these machines. For instance, for use with the CS-3000®, there are available the Fenwal Disposables Nos. 4R2230 and 4R2210. As described in U.S. Pat. No. 4,526,515, for example, these disposables contain a first receptacle useful as a separation chamber, and a second receptacle useful as a collection bag. Typically the commercial plastic disposable insets can be purchased with or without preattached saline, anticoagulant supplies, and aphresis needles for use in continuous processing and return of blood to a patient.

From the mixing chamber the particle/cell conjugate passes to a chamber means contained within the plastic inset wherein separation is effected based upon the difference in the sedimentation velocities of the particle/cell conjugate and the remainder of the cells making up the heterogeneous cell mixture. The unbound fraction can be passed to a second, collection chamber means for collecting the product while the bound fraction is retained in the separation chamber. Alternatively, when the invention is used to capture a therapeutic cell population, the particle/cell conjugate fraction can be captured in the separation chamber, and the cell mixture depleted of target cells can be retained in the collection chamber and returned to the patient. The collection chamber is also contained within the plastic inset and can be placed either within the centrifuge or outside of the centrifuge, depending upon the amount of heterogeneous cell mixture to be processed.

In an alternative and preferred embodiment, the cell mixture and affinity particles are introduced directly into a mixing chamber means in continuous flow, either as separate streams or mixed as a single stream. The mixing chamber means is located within the centrifuge wherein shear forces are controlled so that formation of stable bonds between the particles and the target cells is enhanced.

It has been unexpectedly found that, in this embodiment of the invention, the centrifugal force within the rotating chamber also acts to substantially enhance intimate contact between the particles and the target cells, overcoming the adverse effects of shear forces created by rotation, so that the bonding reaction forming the particle/cell conjugate occurs readily, instantaneously in some cases, within the centrifuge. For this reason the time needed for incubation of the particles is eliminated. Therefore, the particles and heterogeneous cell mixture can be fed into and removed from the centrifuge at the continuous flow rate that would normally be used to separate any component from the heterogeneous cell mixture without substantially increasing the residence time in the centrifuge to allow an "incubation" period for formation of the particle/cell complex.

In some cases, for instances in separation of a leukocyte target cell from whole blood, it is preferred to perform a preliminary centrifugation step without the use of particles. In this preliminary step, those cell populations naturally characterized by a density different than that of others in the cell mixture can be removed before the immunoaffinity separation is undertaken. For instance, with whole blood, an initial centrifugation step can be used to separate the red blood cell population from the leukocytes. Then, in a second step the leukocyte mixture can be treated as the heterogeneous cell mixture used in the continuous centrifugation immunoaffinity separation method.

In other cases, such as the separation of stem cells from a heterogeneous cell mixture, the concentration of the target cell is too limited to use the preliminary centrifugation step, which would fail to capture a significant fraction of the target cells in the concentrate. Greater efficiency of target cell separation can be achieved in this case by utilizing a single step continuous centrifugation immunoaffinity separation.

Particles used for continuous centrifugation immunoaffinity separation are selected and/or designed not only to bind to the target cell population with great specificity, but also to sufficiently alter the sedimentation velocity of the particle/cell conjugate during centrifugation so that continuous separation by centrifugation is possible. The particle selection process is described in detail on pages 18–20, infra. In the centrifuge, the particle/target cell conjugates are directly separated from the other components in the cell mixture by the operation of centrifugal force and their altered sedimentation velocities, with or without the use of a density gradient medium. The decision whether to employ a density gradient medium will depend upon how different the sedimentation velocity of the particle/cell conjugate is from that of other cell populations in the cell mixture as determined by means well known in the art.

The remainder of the cell mixture can either be discarded or returned to the patient, as desired. Depending upon the type of commercial separator machine used, continuous reinfusion to the patient can proceed simultaneously with the continuous separation method herein. It is the particular advantage of the continuous centrifugation immunodensity separation method taught in this invention that large volumes of cell mixture can be processed in a closed, continuous flow on-line procedure with a patient while all blood components not captured by the particles are returned to the patient without any risk of contamination.

As a protective measure, a particle capture device preferably is employed: downstream of the centrifugal cell separator to remove any residual particle/target cell conjugates and/or particles from the remainder of the cell mixture before it is returned to the patient. The particle capture device, usually either a filter or a magnetic device (if the particles used contain magnetic or ferromagnetic materials) is typically located along the downstream portion of the integral, disposable plastic inset used in the centrifugation step. If the capture device is a magnet, the downstream portion of the plastic tubing inset is provided with means for passing the remainder of the cell mixture in close proximity to the magnet so that any remaining particles are retained in a fixed location as remaining, unbound portions of the cell mixture are removed from the location. Such a device is described in U.S. Pat. No. 5,536,475.

If desired, the particle/target cell conjugates recovered from the centrifugal cell separator can be processed to release the particles from the target cells using known methods. For instance, a chemical process, such as reducing a disulfide bond linkage, an enzymatic process, such as proteolytic treatment with a clinical grade preparation of chymopapain, i.e. Discase, or with a growth factor like interleukin 2 or hematopoietic growth factors can be used to expand and release target cell populations from particles. Alternatively, a competitive process such as free antigen or ligand or a physical process such as dissolving the particle from the target cell, or physically removing it by shear forces or energy transfer are contemplated. If the particles are recovered intact, they can be recycled and reused, if desired.

The principal of separation employed in the new technology is the selective alteration of a target population's sedimentation velocity. The sedimentation of cells can be described by Stoke's equation for the settling of a sphere in a gravitational field:

$$V = \frac{d^2(os - oL) \times g}{18N}$$

where V=sedime on rate or velocity of the sphere; d=diameter of the sphere; os=sphere density; oL=liquid density; N—viscosity of the liquid medium; and g=gravitational force. From Stoke's equation, it can be seen that the rate of sphere sedimentation is proportional to the size of the sphere; the sedimentation rate is proportional to the difference in density between the sphere and the liquid; the sedimentation rate is zero when the sphere density is the same as the liquid density; the sedimentation rate decreases as the liquid viscosity increases; and the sedimentation rate increases as the gravitational force increases.

In applied cell separation the sphere represents the target cell population. The binding of particles to the target cell increases its effective diameter, thereby altering its sedimentation velocity. An additional change to the sedimentation velocity can be accomplished by selecting particles that are either more or less dense than the target cells. In this way the sedimentation velocity of the target cell can be made to be greater or less than that of non-target cells. Moreover, the efficiency of cell separation can be altered by selecting different g forces (i.e., by altering the speed of the rotor and/or varying the radius of the rotor in the separation chamber), different liquid medium density, and different times of exposure to the g force i.e., by adjusting the flow rate of the cell suspension containing the conjugates through the sedimentation chamber.

BRIEF DESCRIPTION OF THE DRAWINGS

The invention will be better understood and appreciated by carefully studying the following detailed description of a presently preferred exemplary embodiment of this invention when taken in conjunction with the accompanying drawings, of which:

FIG. 1 is a schematic diagram of a portion of an exemplary continuous flow centrifugation system having a mixing chamber located outside of the centrifuge.

FIG. 2 is a schematic diagram of a portion of an exemplary continuous flow centrifugation system wherein the immunoaffinity particles are metered into a stream of the mixture to be separated and passed into a container located within the centrifuge for binding to the target particle therein.

DETAILED DESCRIPTION OF THE PREFERRED EMBODIMENT

In this invention, a method is provided for on-line, continuous flow selective separation of a specific target cell population from a heterogeneous cell mixture having at least one extraneous cell population with a density and/or sedimentation velocity too close to that of the target cell population to efficiently use known methods of continuous flow centrifugation separation. As a first step, the heterogeneous cell mixture can optionally be subjected to a means, such as a continuous flow centrifuge, for separating a selective cell concentrate based upon the physical properties of the concentrate, thus yielding from the heterogeneous cell mixture a selective cell concentrate. Usually all cell populations in the selective cell concentrate, including the target cell population, will have similar sedimentation velocities. As described above, the initial separation can be effected using any of a number of known and/or commercially available on-line, continuous flow centrifuges for processing large volumes of heterogeneous cell populations. The selective cell concentrate thus obtained is then preferably used as the feed in the method of continuous centrifugation immunoaffinity separation described herein.

The particle means have chemically attached thereto, preferably by means of a covalent or a high affinity bond, a biologic substance capable of binding only the desired cells to the exclusion of other cells. Examples of such bonded substances include antibodies, antigens, proteins generating immune responses, nucleotides, glycoproteins, polysaccharides, lipopolysaccharides, and hormones.

Descriptions of such binding effects are found in numerous publications. T cells and B cells taken from patients with systemic lupus and a variety of other rheumatologic diseases where anti-DNA antibodies are present can bind DNA, Bankhurst, A. D. and Williams, R. C. Jr., "Identification of DNA-binding Lymphocytes in Patients With Systemic Lupus Erythematosus", *Journal of Clinical Investigation*, 56: 1378–1385 (1975). This property is specific to those cells which recognize DNA as an antigen, and is the case with a variety of antigens where the antigen specific T cells and B cells carry receptors for those antigens.

It has also been demonstrated that certain hematopoietic progenitor cells bind specific sugars preferentially, Aizaw, S. and Tavassoli, M., "Molecular Basis of the Recognition of Intravenously Transplanted Hemopoietic Cells by Bone Marrow," *Proceedings of the National Academy of Sciences* 85: 3180–83 (1988).

Additionally, it has recently been shown that a series of proteins known as "selecting", which also bind sugars, have been discovered in certain leukocytes, Lasky L. A. "Selectins: Interpreters of Cell-Specific Carbohydrate Information During Inflammation", *Science* 258: 964–969 (1992). The selectins mediate the selective adherence of these particular leukocytes to blood vessel walls.

This binding phenomenon has also been demonstrated for hormones. Specifically, human growth hormone, a peptide hormone, has successfully been bound to human peripheral lymphocytes, further demonstrating potential uses for the present invention, W. Kiess and O. Butenandt, "Effect of Enzyme and Enzyme Inhibitors on Specific Binding of HGH to Human Peripheral Lymphocytes", *Acta Endocrinologica* 109: 139–144 (1985); Smal, Jean et al. "Receptor-Binding and Down-Regulatory Properties of 22,000-MW Human Growth Hormone and Its Natural 20,000-MW Variant on Im-9 Human Lymphocytes", *Journal of Biochemistry* 225, 283–289 (1985); Eshet, R., Peleg, S. and Laron, Z. "Direct Visualization of Binding, Aggregation and Internalization of Human Growth Hormone in Cultured Human Lymphocytes", *Acta Endocrinologica* 107: 9–15 (1984).

Finally, this binding phenomenon can also be found in the case of lipopolysaccharides (endotoxins). The CD14 antigen found selectively on blood monocytes has been shown to be a receptor for endotoxin.

This binding technique can also be used with any proteins against which the host cell generates an immune response. B cells or T cells specifically reactive to those antigens can be selected out from the heterogeneous mixture. This includes a broad spectrum of protein, nucleic acid, and carbohydrate antigens.

Additionally, any protein having a specific cell surface receptor could potentially be used to selectively remove or harvest reactive cells from a complex mixture of cell types. These include, for example, IgG where specific receptors for this antibody exist on monocytes, neutrophils, B cells, and T cells, Titus, J. A., Sharrow, S. O., and Sagal, D. M. "Analysis of Fc (IgG) Receptors on Human Peripheral Blood Leukocytes by Dual Fluorescence Flow Microfluoremetry", *Journal of Immunology* 130: 1152–1158 (1983).

The binding process could also be used with cytokines such as interleukin 2 or interleukin 1, where specific receptors have been identified on T cells, Smith, W. B., Gamble, J. R. and Vadas, M. A., "Cytokines in the Inflammatory Responses", *Interferons and Cytokines* 21: 26–29 (1992).

The present invention is also applicable for growth factors such as stem cell factor (C-kit ligand), etc., where cell surface receptors have been identified on hematopoietic progenitors, Papayannapoulou, T., Brice, M., Broudy, V. C., and Zsaebo, K. M., "Isolation of C-kit Receptor-Expressing Cells from Bone Marrow, Peripheral Blood, and Fetal Liver: Functional Properties and Composite Antigenic Profile", *Blood* 78: 1403–1412 (1991).

The criteria for use of a given component to bind to cells and allow for differential selection and separation of these from a mixture of cells is that the affinity or avidity of the cell binding to the particle is in excess of the forces acting against the maintenance of this complex. This includes such forces as cell buoyancy, shear force, etc. Thus, any cell particle complex that can be maintained during centrifugation through a ligand-receptor interaction is a candidate for this continuous flow process of cell selection.

The heterogeneous cell mixture, which may comprise a cell concentrate obtained as above described, is intimately contacted with the particle means having a chemically attached biologic substance, bound by either a covalent or a strong ionic bond, to enhance formation of the particle/cell conjugate by binding of the biologic substance to a receptor site on the target cell. Formation of a cell concentrate is preferred because the target cell population to be separated is present at higher concentration than in the original cell mixture. A higher concentration of target cell population tends to favor separation kinetics because numerous unwanted cell types can usually be greatly reduced in number by the preliminary, typically centrifugal cell separation process, thereby greatly reducing non-specific cell reactions. For example, the collection of a lymphocyte cell concentration with minimal red blood cell, platelet, and granulocyte contamination may be effected using a blood cell separator. The separation times in the subsequent centrifugation step are usually reduced and the number of cell types in the concentrate is fewer so that the final product has fewer undesirable contaminating cells.

In one embodiment of the invention, the cell mixture or concentrate is incubated with the particle means in a mixing zone located outside of the centrifuge for a time sufficient to permit selective binding of a specific cell population from the cell mixture to the particles, thereby creating the particle/cell conjugate. In another embodiment, however, the cell mixture or concentrate and the particle means are introduced together into a mixing chamber located within the centrifuge so that intimate contact of the particles is substantially enhanced by the action of centrifugal forces thereupon. But preferably the particle means are introduced as a stream fed slowly or metered into any conduit or passage through which the cell mixture or concentrate is flowing without the use of a separate mixing zone. It has been discovered that in the latter two methods the time required for incubation can be so reduced that formation of the conjugate occurs virtually upon contact. For this reason, the particle means and the cell mixture or concentrate can be continuously fed into the mixing chamber within the centrifuge at the desired centrifugation flow rate.

Using one variation of the latter method, therefore, confers the considerable advantage that blood, or other bodily fluid, from a patient can be continuously withdrawn at any safe and customary rate by means of an apheresis needle attached to the disposable plastic centrifuge inset, and transferred directly into a mixing chamber within the centrifuge along with the particle means for formation of the conjugate. Then the conjugate can be transferred sequentially through the separation and collection chambers at substantially the same flow rate as it was withdrawn from the patient for separation and collection of the particle/cell conjugate. Meanwhile the remainder of the patient's blood can be reinfused as a final step in the continuous process via a second apheresis needle attached to the disposable plastic inset.

Since the particle/cell conjugates will have significantly different sedimentation velocity than those of the remainder of the cells, the particle/cell conjugates can be readily separated from the other cells during centrifugation. However, when it is desirable to ensure that all unbound and bound particles have been removed from the cell mixture—for instance when blood is being continuously processed on-line and reinfused into a patient—one may use magnetic or paramagnetic particles and effect a secondary separation step by routing the return flow of the cell mixture in close proximity past a magnetic means. Alternatively, if the particles used are of a size suitable for capture by a filter, the return flow can be passed through a suitable filter to capture residual particles and particle/cell complexes. In the secondary separation step any remaining particles are held stationary by the magnet or filter while the remainder of the cell mixture flows onward and ultimately returns to the patient unimpeded.

After separation of the particle/cell conjugate from other cells, as described above, the target cell population can be freed from the particles or vice versa, for example by eliminating the bond between the particles and the cells in a known manner, so that a purified, selected population of cells may be provided for further use. For example, target cells may be cleaved using an enzymatic reaction, a reducing agent in the case of a disulfide bond, or a competitive inhibition reaction between the desired protein and the target cell surface. Alternatively, the unbound cells may be the desired cells, being removed from the particle/cell conjugates.

It is also preferred for the container which contains the particle means to be aseptically connected to a flexible, multiple-chamber insert for the blood cell separation centrifuge, so that freshly collected blood cells, or other bodily fluids, can be aseptically combined in the mixing chamber, without any need of forming a sterile connection there between. This greatly simplifies the use in accordance with this invention, and also increases the likelihood that there is no breach of aseptic conditions.

Further in accordance with this invention, one method by which the invention can be practiced includes the following steps. Blood from the patient is either collected in a first container or the patient can be connected to a blood separation centrifuge, the centrifuge being operated to form a cell concentrate which is collected in the first container. The first container is usually sealed until separation of the target cell population is desired. If the particle means are not already in the container, they can be placed in the container in some aseptic manner before the separation step. It is usually difficult or impossible to determine the number of target cells in a heterogeneous cell mixture. However, the number of nucleated cells can more readily be obtained by known means. Therefore, sufficient particle means are used to create a ratio of particle means to nucleated cell population in the range from about 1:1000 to 1000:1, and more preferably from about 1:100 to 100:1. If desired, the particles can be sealed into an inner container positioned within the first container so that the inner container can be broken from outside of the first container to cause release of the particles into the first container.

More commonly, as illustrated in FIG. 1, the cells and the particle means are introduced into a first container 1 used as a mixing chamber where they are mixed by any known means (not shown) and allowed to incubate for a period of from 5 minutes to two hours. Then, the mixing chamber 1 is connected, if not already integrally connected, to the inlet 3 of a clamped disposable separation inset 5 to a continuous flow centrifuge 7 and the disposable inset is placed into the centrifuge 7.

More preferably, however, the incubation step is omitted. As shown in FIG. 2, in this embodiment of the invention first container 1 is located within centrifuge 7 along with the disposable separation inset 5, rotation of the centrifuge is started, and the particle means and blood from the patient are passed aseptically into the first container 1 either as a mixture or as two separate streams. For instance, as illustrated in FIG. 2, the particle means (represented by solid black circles), contained in a light density fluid medium (represented by small specs), can be metered from source 9 by means of metering device 11 into a flowing stream of blood in inlet 3. Blood is shown entering the inlet, and is comprised of a light density fluid component (represented by small specs), a medium density component (represented by triangles), a heavier density component (represented by open squares), and a target cell component within a similar density range (represented by open circles). These target cell components become specifically bound to very heavy density particles (represented by solid circles) that pull the target cell with it to the bottom of container 1. By density centrifugation the particle/cell complex is captured in container 1 by means of centrifugation. The light density fluid component (specs) and the medium density component (triangles) both pass by means of outlet 15 into a second container 17 also located within centrifuge 7. The heavier density separated component (squares) is removed through conduit 5 leaving the centrifuge by means of outlet 13. The medium density components (triangles) are centrifuged to the bottom of container 17. The light density fluid component, typically fluid medium from source 9 and plasma contained in the blood entering through inlet 3, then pass through outlet 13 and can be filtered or passed by a magnet to remove residual particles, based on size or magnetic properties, and returned directly to the patient or donor.

A complete, detailed description and illustration of a centrifugal liquid processing system is shown in U.S. Pat. No. 4,146,172 to Cullis, et al., which description is incorporated herein by reference.

The heterogeneous cell mixtures or concentrates contemplated for use in the practice of this invention are not limited to those derived from whole blood. For instance, a bone marrow preparation can be used in which the cells may be further concentrated and processed in a cell concentrating centrifuge or the like. Additionally, heterogeneous cell mixture can be a tissue-derived cell suspension, or a cell concentrate prepared from peripheral blood using such a centrifugal device. Examples of the latter are concentrates of platelets, lymphocytes, granulocyte, monocytes, or peripheral bone marrow stem cell preparations prepared with a blood cell separator such as the previously described CS-3000® Blood Cell Separator or the Autopheresis-C® System device.

The beads or particles of the particle means can be composed of any number of different materials such as polystyrene latex, plastic copolymers, glass, synthetically produced gel beads and the like. Preferably, such materials will possess good mechanical properties to prevent flaking or fracturing of the beads or particles, and will allow chemical covalent attachment with ease.

The beads or particles can contain a paramagnetic particle such as magnetite to allow separation of the bead or particle/cell conjugate using magnets, as described above. For example, particles may be produced in accordance with the methods as described in U.S. Pat. No. 5,091,206 of Chaeo-huei, J. Wang, et al., (which is a divisional of Ser. No. 113,294, filed Oct. 26, 1987, now abandoned) entitled "Process for Producing Magnetically Responsive Polymer Particles and Applications Thereof."

Suitable particles for use in the practice of this invention are those that when bound to the target cell will alter the physical properties of the particle/target cell conjugate sufficiently that it can be separated from non-target cells during a continuous flow centrifugation process on the basis of its size, density, magnetic, paramagnetic or electrostatic properties or a combination of two or more of these physical properties. Preferably, the sedimentation velocity and/or density of the particle/cell conjugate is sufficiently altered to enhance continuous flow centrifugal separation of the particle/target cell conjugate from a heterogeneous cell suspension containing other particles of similar density, preferably without the use of a density gradient separation media.

However, if desired, any of a variety of known and commercially available density gradient media, such as FICOLL-PAQUE® or PERCOLL® might be used to facilitate this separation. PERCOLL® is a density gradient consisting of colloidal silica particles (15–30 mm diameter) coated with non-dialyzable polyvinylpyrrolidone (PVP). PERCOLL® gradients can be formed within the density range of 1.0–1.3, and are iso-osmatic throughout. FICOLL-PAQUE® is an aqueous solution of density gradient 1.077±0.001 g/ml, consisting of 5.7 g. "Ficoll 400" and 9 g sodium diatriozate with calcium EDTA per 100 ml. The density and osmolarity are optimized for the isolation of lymphocytes from whole blood.

Further, the particles must either possess an inherent tendency to form a chemical bond with the target cell, or they must be capable of attaching thereto, preferably by means of a covalent bond, a biologic, such as an antibody having an active site that will spontaneously and specifically bond with an antigen on the surface of or attached to the surface of the target cell. The reaction between the particle and the target cell is the basis by which particles exhibit specificity for the target cell population. The reaction involves a receptor and a ligand and can be located at various sites within the inchoate conjugate. Examples of the types of ligand/receptor cell interactions that can be employed are listed below wherein p=particle; polyAB= polyclonal antibody; mAB=monoclonal antibody; PrA= Protein A or Protein G; AG=antigen; AV=avidin; B:=biotinylated; CSR=cell surface receptor; PE=peptide or protein, and/=bond. For instance, P-polyAB/mAB/Ag- target indicates a ligand/receptor binding conjugate consisting of polyclonal antibody bound to a particle that binds a monoclonal antibody that can bind to an antigen present on the target population. In the preferred continuous flow process described below, the particle has already been prepared to bind directly to an antigen, carbohydrate, or cell surface receptor on the target cell. Alternatively, the particle can be prepared to bind to an intermediate in the binding conjugate and the target can be pretreated with the remaining components of the conjugate needed to complete the ligand/receptor bond upon contact. This type of ligand/receptor bonding, when used to separate target cells is called bioselective or immunoaffinity separation.

The methods of immunoaffinity separation using monoclonal antibodies, sheep erythrocyte resetting, and the like, are well known, and any of the known naturally occurring and synthetically activated affinity separation particles can be employed so long as the particle possesses the capacity to alter the density and/or sedimentation velocity of the target cells. The methods of activating particles for use in affinity separation techniques are also well known. See, for example, U.S. Pat. No. 4,797,475 to Terasaki entitled "Method and Composition for Isolating White Cell Elements" and U.S. Pat. No. 4,415,665 to Mosbach entitled "Method of Covalently Binding organic Substances to Polymeric Substances," whose teachings are hereby incorporated by reference in their entirety. If it is desirable to use magnetic separation techniques to assist in separating the particle/target cell conjugates from other constituents of the suspension or to assist in recovering the particles before the suspension is returned to the patient, the composition of the particles will be selected to include a magnetic or paramagnetic metal. The DYNAL® Company of Oslo, Norway manufactures paramagnetic microbeads which may be used in accordance with this invention.

As previously stated, the particular biologic materials that can be attached to the particle include antibodies, antigens, proteins avidly bound by cells, glycoproteins, polysaccharides, or lipopolysaccharides. The material may also be a nucleic acid, a lipid molecule, or a synthetic or chemically modified component of such a substance having a selective binding affinity for the cell population to be separated. The methods used for the chemical covalent attachment of biologic materials are known and used in the production of coupled matrix material for affinity chromatography and other selective adsorption applications. Examples of such techniques of covalent attachment to sepharose, gelatine, or other beads may be seen from the following articles: Habeeb, "A Novel Preparation of Immunoadsorbents," *Biochimic et Biophysica Acta*, 673 (1981) 527–538; Cambier, et al., "Isolated Phosphorylcholine Binding Lymphocytes. I. Use of a Cleavable Crosslinking Reagent For Solid-Phase Adsorbent Isolation of Functional Antigen Binding Cells," *Journal of Immunological Methods*, 51 (1982) 209–221; and Bonnafous, et al., "Ligands Immobilized Through Cleavable Mercury-Sulfur Bonds.: *Journal of Immunological Methods*, 58 (1983) 93–107.

The particle means of this invention can be suspended in a buffered salt solution, optionally containing a protein such as albumin, selected to be compatible with the physiological requirements of the heterogeneous cell concentrate and the biological binding material attached to the particle means. The chemical properties of the solution can also be selected to confer sterility to the substance covalently attached to the bead or particle. Furthermore, the solution can have chemical properties selected to favor the formation of the bead or particle conjugate when the cell mixture and the particles are combined.

As will be seen from the following examples, the technology is extremely flexible and numerous equivalent alternatives will be apparent to one who is skilled in the arts of immunoaffinity and centrifugal cell separation. Examples of the type of conjugates having one or more ligand/receptor reaction sites that can be employed include, but are not limited to the following:

A. antibody/antigen reactions P-polyAB/mAB/Ag-target; P-mAB/mAB/Ag-target; P-mAB/polyAB/Ag-target P-polyAB/Ag-target; P-mAB/Ag-target B. Avidin/biotin: antibody/antibody/antigen P-AV/B:polyAB/mAB/AG-target P-AV/B:mAB/nAB/Ag-target P-AV/B:polyAB/Ag-target P-AV/B:mAB/Ag-target C. lectin/carbohydrate P-AV/B:lectin/carbohydrate-target P-Carbohydrate/Lectin-target P-Lectin/target D. Peptide/Cell Surface Receptor (CFR) P-pep/CSR-target E. Protein A (or Protein G)/antibody/antigen P-PrA/polyAB/Ag-target P-PrA/mAB/Ag-target P-PrA/polyAB/mAB/Ag-target P-PrA/mAB/Mab/Ag-target The linkage between the particle and the target cell formed by the ligand/receptor conjugate must be sufficiently stable to withstand the separation process. Also, the ligand/receptor interaction must be sufficiently specific to provide a high degree of separation of the target cell population from the heterogeneous cell suspension. For positive cell selection, the ligand/receptor conjugate bond can, if necessary, be severed to release the target cell from the particle, but care must be taken to use an appropriate chemical or physical means that does not harm the product.

Suitable particles that can be modified as above described include, but are not limited to, the following list: organic and inorganic materials (such as polymers impregnated with metal, porous silic gel, polystyrene, polyethylene, polypropylene, polyacrylamide, metal, and glass), proteins (such as gelatin or albumin), activated carbohydrates (such as cellulose, agarose, or dextran activated with, for instance, p-toluenesulfonyl chloride or 2, 2, 2, -trifluoroethanesulfonyl chloride) bacteria, and liposomes.

The size of the particles is preferably from about 0.1 to 500, more preferably 0.3 to 80 microns in diameter or effective diameter, if the particles are not symmetrical. The density of the particles is preferably from about 0.25 to 5.0, more preferably 0.5 to 2.5 grams per cubic centimeter. The particles can be added in a liquid suspension to promote efficient particle/cell interaction.

On the order of 10 ml. of such liquid suspension, typically including one hundred thousand to 20 billion particles, may be introduced into the mixing zone, for instance a disposable plastic mixing container that is to receive the cells for separation. If it is undesirable of the particles to remain in the mixing container, for example, due to interaction with the wall of the container, they can be added separately by conventional means such as a sterile connector. Alternatively, the particles can be held within a frangible inner container within the mixing container, as above-described, so that the particles enter the interior of the mixing container when the frangible inner container is broken.

As stated above, the various containers used in this application are preferably integrally linked together in their initial manufacture and are sterilized as a unit to avoid the need for sterile connection during processing in accordance with this invention. However, they may also be connected together with sterile connectors, numerous designs which are well-known, for example, those of U.S. Pat. No. Re. 32,056.

The following examples and the other disclosure of this application are provided for illustrative purposes only, and are not intended to limit the scope of the invention, which is as described in the claims below.

EXAMPLE 1

An experiment was conducted to generate a mononuclear cell preparation depleted of a specific leukocyte subpopulation. The cell population selected for depletion was CD4+ lymphocytes. In this experiment, the immunoaffinity particles and blood were incubated together prior to entry into the centrifugal cell separator.

Sheep anti-mouse IgG paramagnetic particles having a density of 1.5 grams per cubic centimeter were purchased from Dynal Inc., located in Oslo, Norway and were coated with anti-CD4 mouse monoclonal antibody (purchased from Becton Dickinson Corp., Mountainview, Calif.) by adding 0.125 ug of antibody per $1 \times 10^7$ beads and incubating overnight at 2–8 degrees Centigrade. ACD anticoagulated whole blood (62 mls. ACD per 450 ml. of blood) was used as the source of CD4+ lymphocytes. Particle/CD4+ lymphocyte complexes were formed by incubating $1 \times 10^{10}$ anti-CD4 Dynal particles and 900 ml. of blood, providing a ratio of 2.2 particles per leukocyte. Incubation was in a closed container at room temperature for 1 hour with end over end rotation at 2.5 rpm.

After the incubation period, the blood/particle mixture was processed using the CS-3000® Blood Cell Separator to generate mononuclear cells. The bag containing the blood/particle mixture was connected to CS-3000® set (Code No.4R2210) via plastic tubing. The volume of the donor blood processed was 0.9 liters. The centrifugal speed was 1,600 rpm and the whole blood flow rate was 60 ml./minute. A granulocyte chamber was used as the separation chamber and a standard Fenwal collection chamber was used to harvest the mononuclear cells. Particle capture was accomplished by density separation within the centrifuge.

The percentage of CD4+ lymphocytes in the unseparated whole blood and in the cells harvested in the collection chamber were determined using a FACSCAN flow cytometer (purchased from Becton Dickinson, Mountainview, Calif.) after staining the cells with fluorescinated mouse monoclonal anti-CD4 (Becton Dickinson, Mountainview, Calif.). In the whole blood, 40.3% of the lymphocytes had the CD4 cell surface antigen. The percentage of lymphocytes in the mononuclear cell bag after depletion having the CD4 cell surface antigen was determined to be only 0.4%. Thus, a 2 log reduction in the percentage of CD4+ lymphocytes was accomplished using the immunodensity technique as a batch continuous centrifugation process.

EXAMPLE 2

The same procedure was followed as in Example 7 except that the anti-CD4 beads and the blood were flowing as two separate streams that were joined via a Y connector which led to the separation chamber so that there was no incubation period of the blood and beads prior to entering the centrifuge. The percentage of CD4+ lymphocytes as determined by the FACSCAN flow cytometer was 46.1% in whole blood but only 3.9% in the mononuclear product bag after depletion of CD-4 cells. Thus, the continuous flow immunodensity technique accomplished a 91.5% reduction in the percentage of CD4+ lymphocytes.

EXAMPLE 3

An experiment was conducted in which blood was first fractionated using a Fenwal CS-3000® blood cell separator into a component rich plasma component containing primarily mononuclear cells (MNC) and a platelet component collected in a transfer pack connected to the appropriate effluent line of the separation chamber. Nine hundred mls. of this MNC preparation was used as the source of CD4+ lymphocytes. Anti-CD4 monoclonal antibody coated Dynal particles prepared as described in Example 1 were added to the transfer pack containing the mononuclear cells and then divided into. two 445 ml. aliquots. Cell separation was achieved with three processes.

Process A:

Continuous Flow Immunodensity Separation. One aliquot of bead/cell suspension was pumped into the CS-3000 collection chamber at a flow rate of 35 ml. per minute. The particle, particle:cell complexes and unbound cells were harvested in the collection chamber. At the end of the run, the contents of the centrifuge collection bag (total volume of 30 ml.) was exposed to a magnetic field to harvest the particles and particle/cell complexes. The cells not captured by the magnetic field were collected and analyzed by flow cytometry.

Process B:

Conventional Rotation Method. The other aliquot of bead/cell suspension was rotated at 11.4 rpm for 72 minutes at room temperature with 3 ml. samples being collected for flow cytometric analysis after 12, 17, 22, 32, 42 and 72 minutes of incubation. At the end of the 72 minutes of incubation, the remainder of the aliquot was processed as described above with the CS-3000®. The 3 ml. aliquots were exposed to a magnetic field to harvest the particles and particle/cell complexes.

Process C:

Rotation Plus Continuous Flow Immunodensity Separation. The 427 ml. of bead/cell suspension remaining after completion of Process B above were then treated according to the description in Process A above.

In summary, the percentage of CD4+ lymphocytes in each sample was determined using a FACSCAN flow cytometer as described in Example 1. The log depletion of CD4+ lymphocytes achieved for each process was 2.85 for continuous flow immunodensity separation (Process A), and a range from 0.61–0.75 after 12 to 75 minutes of incubation for the conventional rotation method (Process B), and 1.89 for the method employing rotation plus continuous flow immunodensity separation (Process C). These data demonstrate the improvement in target cell capture that can be achieved using the invented process as compared to the conventional process of blood separation using magnetic separation alone.

The foregoing detailed description has discussed only several illustrative embodiments or examples of the present invention. Those skilled in the art will recognize that numerous other embodiments, or additions, modifications, deletions and variations of the described embodiments can be made without eliminating the novel and unobvious features and advantages of the present invention. It is intended that all such other embodiments, modifications, deletions and variations be included within the scope of the following claims.

What is claimed is:

1. Apparatus for separating a biological component from a biological fluid comprising:

a rotor comprising a first zone for receiving a biological fluid including a specific biological component and a second zone for receiving a separated portion of said biological fluid from said first zone;

said rotor adapted for creating a centrifugal force field within said first and second zones;

a flow path communicating with said first and second zones for removing at least a portion of said biological fluid from said first zone and introducing said portion into said second zone;

a source of particles located outside of said rotor, said particles having a binding site for selectively binding to said biological component; and means for aseptically and continuously introducing said particles into said first zone.

2. Apparatus of claim 1 wherein said rotor comprises a centrifuge and said chamber is disposed within said centrifuge.

3. Apparatus of claim 1 comprising multiple chambers and means for establishing flow communication therebetween.

4. Apparatus of claim 1 wherein said means for introducing said particles into said chamber comprises a conduit joined in flow communication with said inlet.

5. Apparatus of claim 1 further comprising a device for metering said particles into said chamber.

6. Apparatus of claim 1 wherein said particle source comprises a mixing chamber for mixing said particles and said cell suspension.

7. Apparatus of claim 1 further including a closed, disposable separation inset comprising said inlet, said outlet and said chamber for receiving said biological fluid.

8. Apparatus of claim 7 wherein said disposable separation inset further comprises said source of particles.

* * * * *